United States Patent [19]
Owens et al.

[11] 4,044,594
[45] Aug. 30, 1977

[54] ULTRASONIC TRACK TESTING CARRIAGE

[75] Inventors: William T. Owens, Elmhurst, N.Y.; Albin A. Davidson, St. Louis Park; Eldrid W. Nelson, Minneapolis, both of Minn.

[73] Assignee: Krautkramer-Branson, Incorporated, Stratford, Conn.

[21] Appl. No.: 707,899

[22] Filed: July 22, 1976

[51] Int. Cl.² .............................................. G01N 29/04
[52] U.S. Cl. ................................................... 73/67.8 S
[58] Field of Search ............... 73/67.8 S, 67.8 R, 67.9, 73/67.7, 67.5 R, 71.5 US

[56] References Cited

U.S. PATENT DOCUMENTS

| | | | |
|---|---|---|---|
| 3,028,751 | 4/1962 | Joy | 73/67.8 S |
| 3,251,220 | 5/1966 | Joy | 73/67.7 |
| 3,442,119 | 5/1969 | Cowan | 73/67.5 R |

Primary Examiner—Richard C. Queisser
Assistant Examiner—Stephen A. Kreitman
Attorney, Agent, or Firm—Ervin B. Steinberg; Philip J. Feig

[57] ABSTRACT

An ultrasonic track testing carriage for movement along rails in operative relationship with a test vehicle is disclosed and includes a pair of wheel frames each having guide means for following the gauge side of the rail and ultrasonic sensing means mounted in working relationship with a portion of the rail for detecting changes in the rail and the position of the sensing means relative to the rail with a main frame disposed between the wheel frames and adapted to be coupled to the test vehicle for movement therewith. Interconnecting means extends between the main frame and each of the wheel frames so as to permit each wheel frame independent freedom of motion relative to the main frame in a plane substantially perpendicular to the gauge side of the rail while simultaneously maintaining parallelism between the wheel frames. The ultrasonic sensing means associated with each wheel frame is adapted to be adjusted in a vertical, lateral and angular plane relative to the rail being inspected.

50 Claims, 4 Drawing Figures

ULTRASONIC TRACK TESTING CARRIAGE

BACKGROUND OF THE INVENTION

The present invention relates to the testing of rail in track by means of ultrasonic energy, and more particularly is concerned with a track testing carriage that permits the proper positioning of the ultrasonic sensing means as progressive testing of successive portions of the rail occurs.

The inventors have found that the prior art ultrasonic inspection systems, such as embodied in U.S. Pat. No. 3,028,751, did not provide the necessary precision control for adjusting and maintaining the ultrasonic apparatus with the necessary degree of orientation relative to the rails.

The testing of rail in-track by means of ultrasonic energy requires that the orientation of the ultrasonic beams with respect to the rail be maintained with some precision while the test vehicle moves along the rail at a variable speed. Specifically certain beams directed at an angle with respect to the vertical must be generally parallel to the longitudinal center line of the rail and in some cases coincident with the vertical center line of the rail cross section. A beam directed to impinge vertically on the base of the rail must be so centered and kept perpendicular to the base thereof.

Generally the distance from the gauge or inside edge of the rail head to the vertical center line of the rail section remains constant over considerable distances along the track but may vary by reason of differences in rail section or due to wear of the rail head. Accordingly to obtain the desired precision testing data, it is necessary to maintain the horizontal position of the ultrasonic transducer with respect to the rail section while being able to vary that position at will, and to maintain the angular position of the ultrasonic transducer with respect to the rail axis constantly, as well as with respect to the vertical axis of the section and to vary same at will.

The two rails of a given track, except as they may be out of repair, are parallel to each other and proceed in straight lines except where intentionally curved. When negotiating such curves or testing along straight stretches of track, the parallelism between the transducer beams and the rail axes and hence with each other is to be maintained, this generally in spite of variations in the gauge (distance between the rail heads) and variations in the straightness of one or both rails. To accomplish these functions the inventors have devised an ultrasonic track testing carriage which provides freedom of motion either voluntarily, or automatically in some senses, while resisting motion in others to obtain the necessary echo signals.

OBJECTS OF THE INVENTION

An object of the present invention is to provide an inspection carriage such that the ultrasonic inspection means associated therewith may be adjusted in a precision manner relative to the rails.

Another object of the present invention is to provide a track testing carriage in which the ultrasonic sensing means associated with each rail may be independently adjusted for vertical, lateral and angular positionment relative to the upper surface of each rail.

Another object of the present invention is to provide an ultrasonic track testing carriage having a main frame with spaced apart wheel frames independently movable relative to the main frame and in a plane substantially perpendicular thereto.

Another object of the present invention is to provide a novel method by which rail track may be inspected using ultrasonic energy with the positionment of the sensing means readily adjustable to conform to the cant of the rail as well as lateral adjustment depending upon the return signals received by the ultrasonic sensing means.

Other objects and advantages will become apparent as the disclosure proceeds.

SUMMARY OF THE INVENTION

The present invention provides a novel combination of steps and elements working together to provide a precision system for the testing of rail track using ultrasonic sensing means. The ultrasonic sensing means may take various forms and shapes, but is responsible for transmitting and receiving pulses of high frequency signals and relies upon the pulse-echo and through transmission principles of flaw detection to determine the specific types of flaws encountered in the rail. The present invention makes use of these ultrasound principles and particularly is adapted to determine the cant of the rail and the wear of the head of the rail as well as flaws contained therein.

In accordance with the invention, an ultrasonic track testing carriage for movement along rails in operative relationship with a test vehicle is disclosed having a pair of wheel frames each having guide means, in a preferred embodiment a pair of spaced apart track-engaging wheels, to follow the gauge side of the rail. A main frame is disposed between the wheel frames and is adapted to be coupled to the test vehicle for movement therewith. Interconnecting means between the main frame and each of the wheel frames is provided and includes one or more pair of link members associated with each wheel frame and the main frame with means for pivotally mounting each pair of the link members in spaced apart relationship to each other between the wheel frames and the main frame. Coupling means is provided for pivotally joining each pair of the link members together to provide a connection therebetween so as to permit each wheel frame independent freedom of motion relative to the main frame in a plane substantially perpendicular to the gauge side of the rail while simultaneously maintaining parallelism between the wheel frames.

Locking means is operatively connected between the coupling means and the main frame to lock the position of the wheel frames in place relative to the main frame. Positioning means is associated with each of the wheel frames, and cant means is mounted relative to each wheel frame in surrounding relationship to the positioning means. Ultrasonic sensing means is mounted on each of the positioning means having a working surface to be placed in operative relationship with a portion of the rail for detecting changes in the rail and the position of the sensing means relative to the rail.

The positioning means includes a positioning frame, with means for mounting the positioning frame relative to the cant frame, wherein the ultrasonic sensing means extends downwardly from the positioning frame, and means for lateral displacement of the positioning frame relative to the cant frame to provide the incremental adjustment of the working surface of the ultrasonic sensing means relative to the rail portion being tested. The cant means includes a cant frame adapted to be positioned within each wheel frame having an upper end and downwardly extending lower end, with means for mounting the lower end relative to the wheel frame along an axis extending substantially parallel to the rail for angular displacement of the cant frame along the axis. Power means extends between the wheel frame and the cant frame at the upper end to obtain lateral displacement between the cant frame and the wheel frame so as to obtain the desired angular displacement of the ultrasonic sensing means for proper positioning relative to the portion of the rail being tested.

The power means extending between the wheel frame and the cant frame at the upper end thereof includes hydraulic means pivotally connected at one end thereof to the wheel frame with a bracket extending from the cant frame, and a piston rod axially extending from the hydraulic means having its free end coupled to the bracket, such that linear movement of the piston rod applies the necessary force to obtain the angular displacement of the cant frame relative to the axis. The means for obtaining lateral displacement of the positioning frame relative to said cant frame includes hydraulic means connected to the positioning frame at each end thereof. The hydraulic means has a piston rod extending axially therethrough and outwardly from each end thereof, with means for mounting each end of the piston rod in fixed relationship to the cant frame such that the hydraulic means moves laterally along the piston rod to obtain the desired lateral adjusted positionment of the ultrasonic sensing means relative to the rail.

The locking means operatively connected between the coupling means and the main frame to lock the position of the wheel frame in place relative to the main frame, operates in conjunction with energizing means operatively associated with the wheel frames to automatically activate said locking means, and includes switching means operatively associated with and mounted relative to the ultrasonic sensing means such that downward movement thereof automatically energizes the switching means such that activation of the locking means locks the position of the wheel frames to prevent lateral movement thereof relative to the main frame.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DETAILED DESCRIPTION OF THE DRAWINGS

Figure 1:
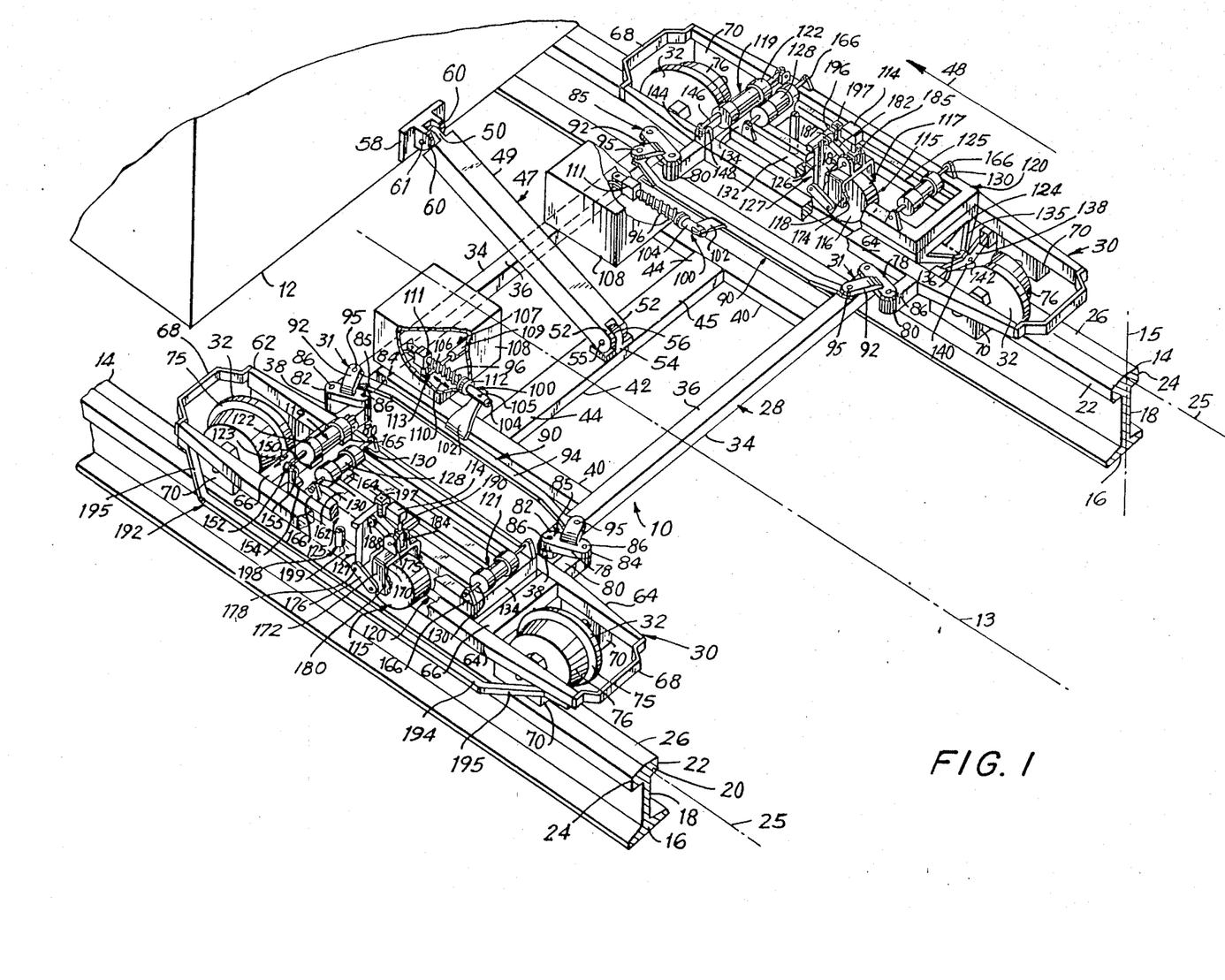
FIG. 1 is a perspective view, partly broken away and in section, of the ultrasonic track testing carriage in accordance with the present invention.
Figure 2:
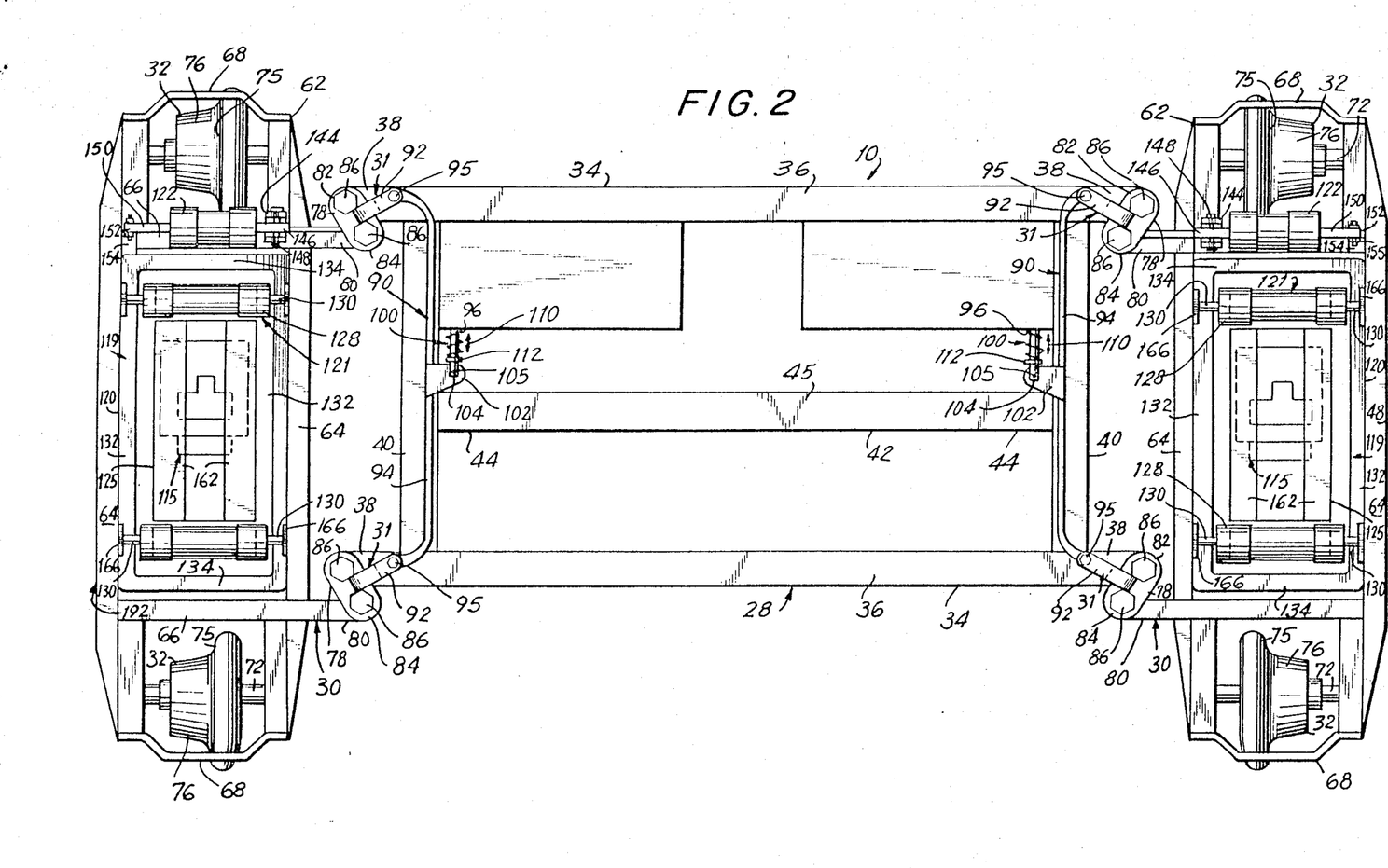
FIG. 2 is a top plan view of the ultrasonic track testing carriage illustrated in FIG. 1.

Referring to the drawings in detail and initially to FIGS. 1 and 2 thereof, there is illustrated a probe truck or carriage 10 that is to be towed or pushed by a testing vehicle 12. The carriage 10, as hereinafter explained, is adapted to determine the condition of the track having a center line identified by numeral 13 which includes a pair of spaced apart rails 14. Each rail 14 has a vertical centerline section identified by numeral 15 with a rail base 16 having a vertically extending web portion 18 that terminates in the rail head 20 having an inner surface or gauge side 22 and a field side 24. The rail head 20 has a rail centerline 25 extending along the longitudinal length thereof. The wheels of the train engage the upper surface or top portion 26 of the rail head 20. The above nomenclature for a rail is well known in the art and the rail 14 may vary in its exact configuration in accordance with the various standards of the industry.

The carriage 10, as hereinafter explained in detail, is adapted to detect various flaws within the rail 14 as well as determine various other characteristics that might require sections of rail 14 to be replaced. The carriage 10 is adapted for movement along the rails 14 in operative relationship with the test vehicle 12. The test vehicle 12 contains the various electronic instrumentation and other controls necessary to regulate the various movements in the carriage 10 as well as means to view the reflected ultrasonic pulses received by sensing means disposed upon the carriage 10 which pulses are converted to electrical signals and transmitted to a cathode ray tube or other device in the view of the operator within the vehicle 12 in a manner well known in the art. Moreover, the test vehicle 12 or carriage 10 includes reservoir means for storing a couplant to be disposed on the upper surface 16 of the rail 14 during testing.

The carriage 10 includes a body or main frame 28 and two side or wheel frames 30 that in turn each carry two spaced apart track wheels 32 for engagement with the spaced apart rails 14. Interconnecting means 31 is provided between each wheel frame 30 and the main frame 28 on opposite sides thereof to permit independent movement with respect to the main frame 28 as hereinafter discussed in detail. The wheel frame 30 may be carried along the rail on a shoe or other means having a flange or other guide means for following the gauge side 22 of the rail 14. The main frame 28 includes a pair of spaced apart horizontal cross supports or members 34 extending transversely to the rails 14 and having an upper surface 36. Each cross member 34 terminates at a terminal end 38. The cross members 34 extend in substantially parallel spaced relationship to each other and are rigidly coupled by frame members 40 which in turn has a center cross member 42 connected at each end thereof 44 to one of the frame members 40. The upper surface 45 of the cross member 42 may extend in the same horizontal plane as the upper surface 36 of the cross members 34.

The main frame 28 may be welded together to form a rigid unitary structure adapted to be centrally disposed between the spaced apart tracks 14 to which the wheel frames 30 are in turn interconnected such that each wheel frame 30 may move independently relative thereto. The main frame 28 is connected to the test vehicle 12 by tow means 47 connected between the main frame 28 and the test vehicle 12 to provide movement of the carriage 10 along the rails in the preferred direction of travel as illustrated by arrow 48. The tow means 47 includes a tow bar 49 having a neck portion 50 at one end thereof and a pair of spaced apart flanges 52 at the opposite end thereof. The tow bar 49 is pivotally mounted to the frame 28 be means of a bearing 54 secured to the upper surface 45 of the cross member 42 and having an axially extending pin 55 extending through the flanges 52 and the neck portion 56 of the bearing 54 extending therebetween.

The bearing 54 is of the compliant type in order to provide several degrees of freedom for the motion of the main frame 28 relative to the towing vehicle 12. The carriage 10 may translate with respect to the vehicle 12, rotate about a vertical axis, rotate about a horizontal axis perpendicular to the track, and rotate about an axis parallel to the track. The carriage 10 also is designed to have certain inherent components of motion that it is capable of exhibiting as it is maintained in position between the rails as it remains in contact with the rails while simultaneously remaining generally parallel to the center line 13 of the track.

A vehicle bearing 58 extends from one end of the vehicle 12 and is adapted to receive the neck portion 50 through a pair of spaced apart neck flanges 60 with a member or pin 61 extending transversely therethrough. The vehicle bearing 58 is also selected of a compliant type in order to permit the necessary degrees of freedom of motion discussed above.

Figure 3:
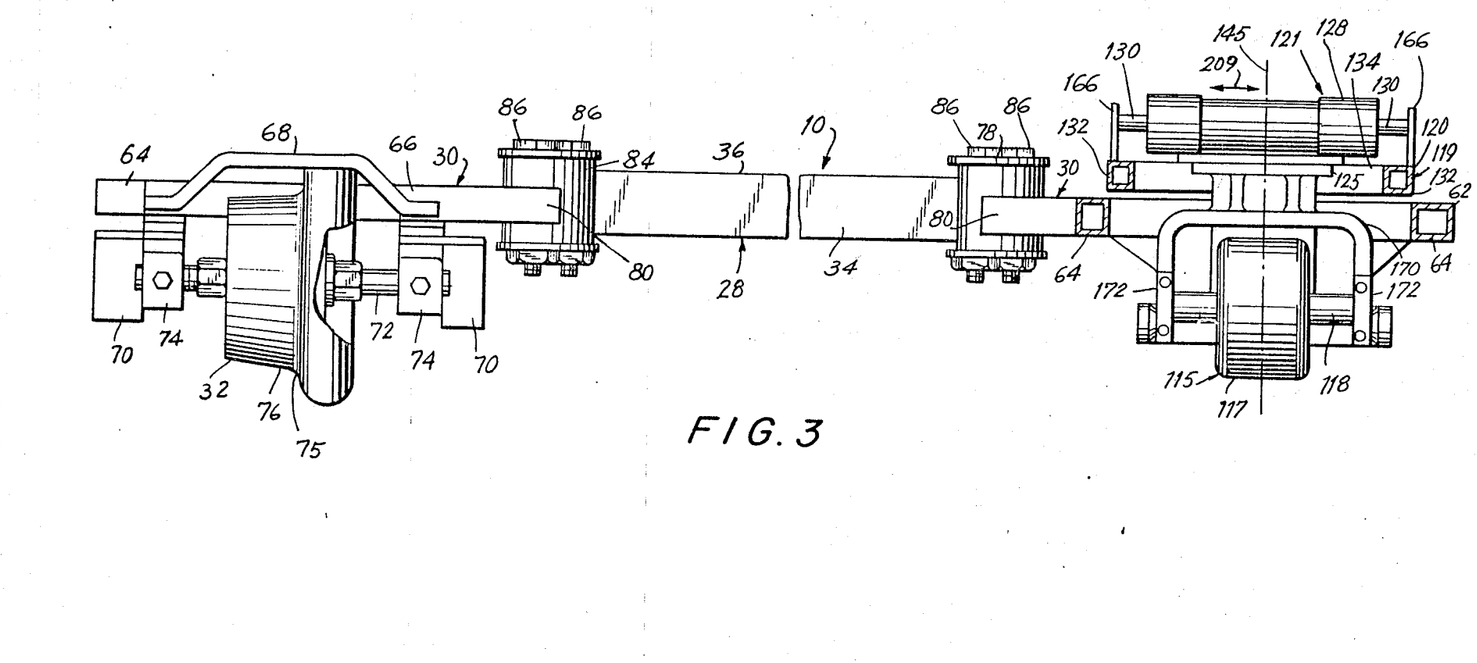
FIG. 3 is a front elevational view of the track testing carriage illustrated in FIG. 2.

The wheel frames 30 each include an outer frame 62 that includes a pair of spaced apart outer frame members 64 that extend substantially parallel to each other as well as the center line of the rail 14. The outer frame 62 further includes outer frame cross members 66 which extend between the outer frame members 64, to form a rigid coupling therebetween. A guard 68 is mounted across each end of the spaced apart outer frame members 64. The wheels 32 are mounted from the outer frame 62 by means of a pair of spaced apart mounting blocks 70 that are coupled to the outer frame members 64. A horizontally extending shaft 72 as seen in FIG. 3 and associated bearing 74 support each respective wheel 32 in a conventional manner well known in the art. Each wheel 32 includes the inner edge 75 for engagement with the gauge side 22 of the rail 14 and a contacting surface 76 which rolls along and engages the upper surface 26 of the rail head 20. In this manner each wheel frame 30 is adapted for rolling engagement with its particular rail 14 associated therewith.

To maintain the proper relationship between the wheel frames 30 and the main frame 28 interconnecting means 31 is provided. The interconnecting means permits each wheel frame 30 to move independently with respect to the main frame 28. The interconnecting means 31 includes a pair of link members 78 adapted to extend about an inwardly disposed link arm 80. As illustrated in FIG. 1, each outer frame member 64 on the gauge side of the rail 14 has a pair of inwardly disposed link arms 80 that may be in alignment with the outer frame cross members 66. The upper end 82 of each link arm 80 may extend in substantially the same horizontal plane as the upper surface 36 of cross member 34. Each link member 78 includes a main frame end 82 and a spaced apart wheel frame end 84. Pivot means 85 are provided in order to obtain the necessary lateral movement between the wheel frames 30 and the main frame 28. The pivot means 85 may include a pivot member or pin 86 that is vertically extending to interconnect the link arm 80 with the link arm end 84 of the link member 78. In similar fashion, the main frame end 82 of the link member 78 is connected to the terminal or outer end 38 of each cross member 34 by the vertically extending pin 86.

As illustrated in FIG. 1, relative to the preferred direction of travel as illustrated by arrow 48, the link arms 80 extend behind the respective cross members 34. With the interconnection as discussed above of the interconnecting means 31, each wheel frame 30 would be free to move at either end thereof relative to the main frame 10. In order to maintain freedom of motion but to simultaneously obtain equal movement of each wheel 32 towards and away from its respective rail 14 in a plane substantially perpendicular to the rail 14, coupling means 90 is utilized. The coupling means connects together, while simultaneously permitting angular movement of the respective link members 78 while maintaining parallelism between the wheel frames 30.

The coupling means 90 includes a coupling element 92 connected to and extending outwardly from each link member 78. As illustrated in FIG. 1, the coupling element 92 is disposed centrally between the pivot pins 86 and includes a coupling arm 94 connecting each respective pair of coupling elements 92 at the outer end thereof as by vertically extending pivot elements 95. This interrelationship of the interconnecting means 31, pivot means 85, and coupling means 90 provide a unison constraint to the wheel frames 30 and permit lateral movement as required during movement of the carriage 10. In this manner a pantograph mechanism has been provided such that each wheel frame 30 may translate with respect to each other and still maintain their parallelism with respect to each other. It is important to permit each wheel frame 30 to move in and out, perpendicularly to the rails 14 while maintaining their orientation with respect to the main frame 28. The above linkage relationship is such that each link member 78 pivots around each link arm 80 and simultaneously about the outer end 38 of each cross member 34. The outwardly extending coupling element 92 which is in turn pivotally connected by the coupling arm 94 provides the necessary mechanical tie between so as to obtain the coordinated but independent movement of each wheel frame 30.

As can be appreciated as the carriage 10 moves along the track the tow means 47 which permits a certain degree of freedom of movement constrains the main frame 28. As this movement occurs, two forces act to cause the individual wheel frames 30 to move outward away from the center of the track. One of these forces is a natural result of the motion of the main frame 28 in the preferred direction of travel and the normal position of the link members 78 with respect to their travel. The wheel frames 30 are towed by the coupling relationship of the link members 78 and the inertia of the wheel frames 30 create a moment about the pivot points of the pivot pins 86 such that the link members 78 rotate toward a position that would place them parallel to the direction of travel.

A second force simultaneously acts in the same direction acting as a bias to the natural force discussed above, and acting in the opposite direction when the carriage 10 is propelled backward opposite to the preferred direction of travel as illustrated by arrow 48.

The second force is caused by a spring 96 mounted in a manner hereinafter described to provide the necessary force to the coupling means 90 which in turn is transmitted to the link members 78. Locking means 100 is operatively associated with the coupling means 90 on each wheel frame 30 in order to lock the position of the wheel frame 30 in place relative to the main frame 28 when required. The locking means 100 includes a locking arm 102 extending inwardly from each coupling arm 94 for receiving a locking element 104 pivotally mounted thereto as by pivot member 105. The opposite end 106 of the locking element 104 is contained within a housing 108 that may be mounted on one of the cross members 34. To activate the locking means 100, energizing means 107 is provided and includes an electromechanical solenoid 109 mounted within the housing 108 and when activated prevents further movement of the locking element 104 in the direction of double-headed arrow 110. The electrical connection to the solenoid 109 is contained within the vehicle 12 on an instrument panel (not shown) for monitoring by the operator thereof.

The spring 96 is mounted in telescopic relationship and abuts a radially extending flange 112 on the locking element 104. The force of the spring 96 as it abuts the radially extending flange 112 acts to move the coupling bar 94 against the preferred direction of travel as illustrated by arrow 48 and consequently to rotate the link members 78 in the same direction as the natural force discussed above.

The locking means 100 referred to above provides an additional function necessary under some circumstances to lock the position of the wheel frames 30 with respect to the main frame 28 when the carriage 10 is lifted from the track and off of the rails 14. In addition, when the carriage 10 must pass through switches, frogs, or other tracks features where lateral restraint normally provided by the rails 14 is nonexistent, then it is desired to freeze the position of the wheel frames 30 during this interval of time.

In accordance with the present invention, the carriage 10 is lifted hydraulically and revolved 90° about the axis of pin 61 taking a vertical position for stowage within a compartment (not shown) in the test vehicle 12. It is during this stowage as well that the function of the locking means 100 is utilized to obtain a fixed relationship between the wheel frames 30 and main frame 28.

The locking means 100 includes a lock mechanism 111 to which the end 106 of the locking element 104 is connected, and which may be in accordance with U.S. Pat. No. 3,874,480, the subject matter of which is incorporated herein by reference. The lock mechanism 107 is normally locked, preventing relative motion between its telescopic members whether induced by the bias spring 96 or by external forces. Each lock mechanism 111 is released by actuation of a lever 113 by the rotary solenoid 109.

Electric power to each solenoid 109 is supplied by switching means which is through two manually controlled switches, one each at the driver's and operator's position in the vehicle 12 and to a limit switch 114 on each wheel frame 30, all connected in series. The limit switch 114 forms the automatic switching means and acts as the signal for the energizing means 107 to activate the locking means 100. In this manner at any time that either wheel frame 30 is lifted from the rail 14 or when the carriage 10 is lifted for stowage, at least one of the limit switches 114, as hereinafter explained in more detail, will open and the solenoids 109 will be deenergized, thus permitting the locking mechanism 107 to assume the "lock" position and prevent movement of the wheel frame 30 with respect to the main frame 28.

Under normal operating conditions restraint is provided by the guide wheels 32 within each wheel frame 30 since the guide wheels 32 are flanged and conform generally to standard rail wheel design practices. The wheels 32 run on the top surface 26 of each rail 14 and due to the outward forces applied to each wheel frame 30 the wheel flanges 75 bear against the inside surface 22, or gauge side of each rail 14. Thus, the position of each wheel frame 30 with respect to its associated rail 14 is maintained.

The relationship of the ultrasonic transducer assembly or sensing means 115 to the plane of the track and to the gauge side 22 of the rail 14 is variable and requires adjustment from time to time. The ultrasonic sensing means 115 is adapted to transmit and receive ultrasonic pulses in a manner well known in the art. The ultrasonic sensing means 115 includes one or more transducer probes for transmitting ultrasonic energy into a rail at one or more preferred angles of incidence. The individual probes are disposed at predetermined spaced locations along the rail and at predetermined angles for detecting flaws disposed at different angles and in different locations in the rail 14. The probes may be carried along the rail in sliding engagement or in one or more wheels. In the present embodiment the center line of the ultrasound beam emitted by a transducer probe in each wheel probe 116 lies in a plane perdpendicular to the axle 118 of the wheel 116 upon which it rotates. To establish the proper angular relationship of the beam with respect to the rail 14, provision is made for rotation of the sensing means 115 about an axis parallel to the longitudinal axis of the rail, provision is also made for lateral adjustment of the beam relative to the gauge side 22 of the rail 14. The wheel 116 has a circular peripheral contacting or working surface 117 adapted to be placed in operative coupling relationship with the upper surface 16 of the rail 14. The surface 117 acts as the energy output and receiving surface for rolling contact with the rail 14.

Accordingly, the desired relationship of the transducer assemby 115 with a horizontal plane, or the plane of the track, and the gauge side 22 of the rail 14 is variable and requires adjustment from time to time. The center lines of the ultrasound beams emitted by the wheel probe 116 lie in a common plane by construction and the plane is perpendicular to the axle 118 of the wheel 116 upon which it rotates. It is necessary to the test function that this plane coincide with the central plane of the rail cross section. Rail is generally laid with a small degree of "cant" toward the inside so that the plane of its section center is not truly vertical nor perpendicular to the plane of the track. Further, due to wear of the top 26, or running surface, of the rail 14 a sound beam entering the rail 14 parallel to the plane of the center line 15 of its section is refracted and is no longer parallel within the rail 14. To establish the proper angular relationship of the beam with respect to the rail, some rotation of the sensing means 115 about an axis parallel to the longitudinal axis 15 of the rail is required. Because of differences in rail head dimensions and wear at the side of the head 20, against which the guide wheels 32 bear the distance between the gauge sides 22 of the rails 14 and the flanges 75, the guide wheel 32 and the central plane of the sound beams must also be variable. Once made, these adjustments must be firmly held.

The adjustment for distance between the rail gauge and the center plane is called the "lateral adjustment", and the angular correction for rail cant and head wear-caused refraction is the "cant adjustment". Accordingly cant means 119 is provided in operative relationship to each sensing means 115 to obtain the necessary tilting thereof. The cant means 119 is associated with each wheel frame 30 and includes a cant frame 120 mounted for angular adjustment relative thereto. The cant frame 120 is supported by two in-line bearings 136 whose axis is parallel to the rail. The cant frame 120 is controlled by the power or cant cylinder 122 which is a double-acting, as indicated by double headed arrow 123, hydraulic cylinder operable to cause the cant frame 120 to rotate about its axis identified by numeral 124. By means of bi-directional switching of hydraulic valves and the application of hydraulic pressure, the sensing means 115 may be positioned at the desired angle with respect to the vertical center line 15 of the rail 14. The operator can observe that this angle has been optimized by observing that the echo received by the sensing means 115 from the base 16 of the rail 14 is at a maximum amplitude as observed on a cathode ray screen or other indicator within his view.

Within the cant frame 120 positioning means 121 is provided and includes a second adjustable member in the form of a positioning frame 125 to which the sensing means 115 is suspended by means of the support means 127 including a bracket 126. The positioning frame 125 is suspended from and connected to the cant frame 120 through a pair of double acting power or hydraulic cylinders 128 secured to the sides of the cant frame 120 and positioned so that any motion of the cylinder body along the piston rods 130 is generally perpendicular to the center line 15 of the rail 14. Adjustment of the positioning means 121 permits incremental lateral adjustments of the ultrasonic sensing means 115 on each wheel frame 30. The lateral position of the positioning frame 125 is remotely caused and observed from the operator's position as with the cant adjustment. Movement of the positioning frame 125 carries with it the sensing means 115 and its ultrasonic beams whose optimum position can be observed as indicated by the maximum amplitude of the base echo.

Alternatively, the cant adjustment and the lateral adjustment can be automatically performed. For example, in U.S. Pat. No. 3,898,838 a method of automatically adjusting a transducer probe in a direction normal to a workpiece surface is disclosed. Also, in U.S. Pat. No. 3,969,926 a further method and apparatus for aligning a transducer probe normal to a workpiece surface employing additional sensing means is disclosed. Either disclosed arrangement, when incorporated in the preset invention, will automatically perform the cant and lateral adjustments without further operator adjustment. Similarly, automatic adjustment means may be used to locate the probes at predetermined spaced locations along the rail.

Referring now more specifically to the cant frame 120, there is provided a substantially rectangular cant support system that includes a pair of spaced apart cant members 132 extending substantially parallel to the outer frame members 64 and a pair of spaced apart cant members 134 joined at each end of the cant members 132. This rectangular frame has downwardly extending therefrom cant pivot members 135 at each end thereof to form the cant pivot frame support having a bearing 136 centrally disposed as illustrated in FIG. 1 through which the cant frame axis of rotation 124 extends. Positioned in operative relation thereto is a wheel frame pivot support member 138 with a centrally disposed bearing 140 adapted to receive a cant pivot pin 142 extending therethrough. This permits angular movement at the upper end of the cant frame 120.

To control the angular movement, the cant cylinder 122 is provided with one end thereof connected in a pivotal fashion to a cant pivot bracket 144, which is secured in fixed relationship to the inwardly disposed outer wheel frame member 64. The cylinder 122 has a fixed arm 146 extending outwardly from one end thereof with a transversely connecting pivot member 148. Extending from the other end of the cant cylinder 122 is the cant piston rod 150 adapted to move in the direction of double headed arrow 123 in relation to the flow of hydraulic fluid therein in a manner well known in the art. The free end 152 of the cant piston arm 150 is pivotally mounted to a cant frame bracket 154 which is secured to the cant member 132 and having a transversely extending cant pivot pin 155 connecting the free end 152 to the bracket 154.

In accordance with the above mounting relationship, the cant frame 120 is controlled by the cant cylinder 122 which may be a double acting hydraulic cylinder. The admission of an incompressible fluid to either port of the cylinder 122 under pressure will cause the cylinder shaft 150 to extent or retract and, in turn, to cause the cant frame 120 to rotate about its axis 124. By the closure of hydraulic valves, one each at each port of the cylinder 122, the entire internal volume of the cylinder 122 and associated piping thereto is full of the incompressible fluid and will lock the position of the cant frame 120 against any forces tending to cause rotation. By means of bi-directional switching of the hydraulic valves and the application of controlled, low-flow hydraulic pressure, the control means being located at the operator's position within the test vehicle, the ultrasonic sensing means 115 of each wheel frame 30 may be placed at the desired angle with respect to vertical center line 15 of the rail 14. The operator can observe that this angle has been optimized by observing that the echo received by the sensing means 115 from the base 16 of the rail 14 is at a maximum amplitude as observed on a cathode ray screen or other indicator within his view.

Referring now more specifically to the positioning of lateral frame 125 mounted for movement relative to the cant frame 120 to further obtain the exact positionment of the ultrasonic transducer means 115 relative to the web 18 of each rail. The positioning frame 125 may be substantially enclosed by the cant frame 120, and includes a pair of spaced apart side positioning support members 162 mounted in substantially parallel spaced relation to the cant support members 132. Lateral or end cross members 164 interconnect the positioning support members 162 at each end thereof to form a rigid frame from which the ultrasonic sensing means 115 depends by bracket 126. The positioning hydraulic cylinders 128 are rigidly connected to the upper end of the positioning frame 125 as by a positioning cylinder base 165 which as illustrated is secured at each end of the positioning frame 125 in overlapping relationship to each positioning cross member 164.

The positioning cylinders 128 ride on their outwardly extending slide piston rods 130 which are firmly secured to positioning support brackets 166, and which extend vertically from the upper end of each cant member 132. A pair of brackets 166 are provided in conjunction with each of the four positioning cylinders 128. This mounting relationship is such that the positioning frame 125 may be laterally positioned through the slide hydraulic cylinders 128 whose piston 130 extends doubly through the seal and bearing at each end thereof so that the piston rods 130 are secured to the respective sides of the cant frame 120 and so positioned that any motion of the cylinder body 128 along the piston rods 130 shall be generally perpendicular to the cant frame axis 124 and hence perpendicular to the center line 15 of the rail 14.

Adjustment of the lateral position of the positioning frame 125 is remotely caused and observed from the operator's position within the vehicle 12 as previously explained with respect to adjustment of the cant frame 120. Motion of the positioning frame 125 also causes the transducer assembly 115 to move a similar distance and with it the ultrasonic beam whose optimum position can be observed as that at which the base echo is at maximum amplitude. In this manner lateral, angular and vertical movement of the sensing means is obtained. The cantmeans 119 as illustrated in FIG. 3 may be tilted or rotated up to approximately 4° in either direction of the vertical centerline 145.

The utilization of the cant frame 120 and lateral frame 125 are uniquely free of instability since there are no linkages or bearings primarily involved in their motion. The incompressibility of the hydraulic fluid within the slide cylinders 128 and cant cylinders 122 provides sufficient force of retention since the respective cylinder and the associated valves and piping are selected having a sealing capability that is generally of an order of magnitude greater than the natural forces which tend to develop.

The ultrasonic sensing means 115 is mounted to have a degree of motion in a plane substantially normal or vertical to the upper surface 26 of the rail 14. To provide this vertical freedom of motion, support means 127 is provided and includes a bracket 126 firmly connected to the positioning support members 162 with a transducer support housing or bracket 170 mounted for the vertical displacement. The housing 170 includes a pair of spaced apart downwardly extending arms 172 that extend on both sides of the transducer wheel 116 and connected by a bearing block 174 to the arms 172 to support the probe axle 118. The upper end of the bracket 170 has a pair of spaced apart support ears 175.

To provide the vertical displacement for rolling contact between the outer working or contacting surface 117 of the wheel 116, lower pivot members 176 are provided and are connected at one end thereof by pivot pin 178 to the lower end of the bracket 126 and at the other end by pivot pin 180 to the transducer housing arm 172. Associated with the ears 175 is an upper pivot arm 182 extending between the ears by a pivot block 184 having an upper surface 185. The pivotal relationship is obtained by transducer pivot pin 186 extending between the ears 175 and the pivot block 184. The other end of the upper pivot arm 182 is similarly pivotally mounted from pivot brackets 187 receiving a pivot pin 188 transversely thereto. In this manner a parallelogram relationship is obtained for vertical displacement with the probe wheel 116. The limit switch 114, previously discussed, has a downwardly extending switch arm 190 for engagement with the contacting surface 185. As previously discussed, if for any reason the sensing means 115 moves downwardly due to an interruption in the rail 14, then the solenoid 109 will be activated such that the locking means 100 prevents outward movement of the wheel frame 30.

To safeguard the carriage 10 when rolling through switches, etc., in order to protect the sensing means 115, there has been provided skid means 192 mounted relative to the outside of each wheel frame 30. The skid means 192 may include an outwardly extending skid member 194 having a tapered pair of spaced apart ends 195 that are welded or otherwise rigidly joined to the outer frame member 64. In this manner the skid member 194 is so positioned to vertically lift the wheel frames 30 and hence the entire carriage 10 including the main frame 28.

When such lifting occurs, the sensing means 115, which is mounted off of the pantograph type bracket 126, remains in contact with the rail 14 for some distance while the bracket 126 moves upwardly with the wheel frame 30. The relative motion between the respective parts of the housing 170 is caused both by the vertically extending pressure spring 196 mounted from a spring bracket 197 for engagement with the pivot arm 182 and the upward movement of the wheel frames 30. The relative motion is such that weight of the wheel 116 causes the limit switch 114 to be deactuated so as to anticipate loss of lateral restraint by the wheel frames 30. As previously explained, the limit switch 114 is electrically connected to the energizing means 107 which in turn activates the solenoid 109 which in turn activates the locking means 100. When the obstruction has been passed in that the skid means 192 is no longer in engagement therewith, the carriage assembly will move downwardly to the point where the limit switch 114 is reactivated thereby releasing the locking means 100 to once again permit freedom of lateral motion between the respective wheel frames 30 due to the inherent motion of the interconnecting means 31.

Fluid supply means 198 coupled to a reservoir (not shown) located either in test vehicle 12 or upon carriage 10 is utilized to continously provide fluid 199 onto the upper surface 26 of the rail 14. The fluid 199 acts to bring the contacting surface 117 of the ultrasonic sensing means 115 in acoustic energy coupling relationship to the upper surface 26 of the rail 14. The fluid supply means 198 is positioned relative to the preferred direction of travel 48 in front of the ultrasonic sensing means 115 for continuously providing such acoustic coupling relationship between the sensing means 115 and rail surface 26 as the sensing means 115 traverses the rail.

Figure 4:
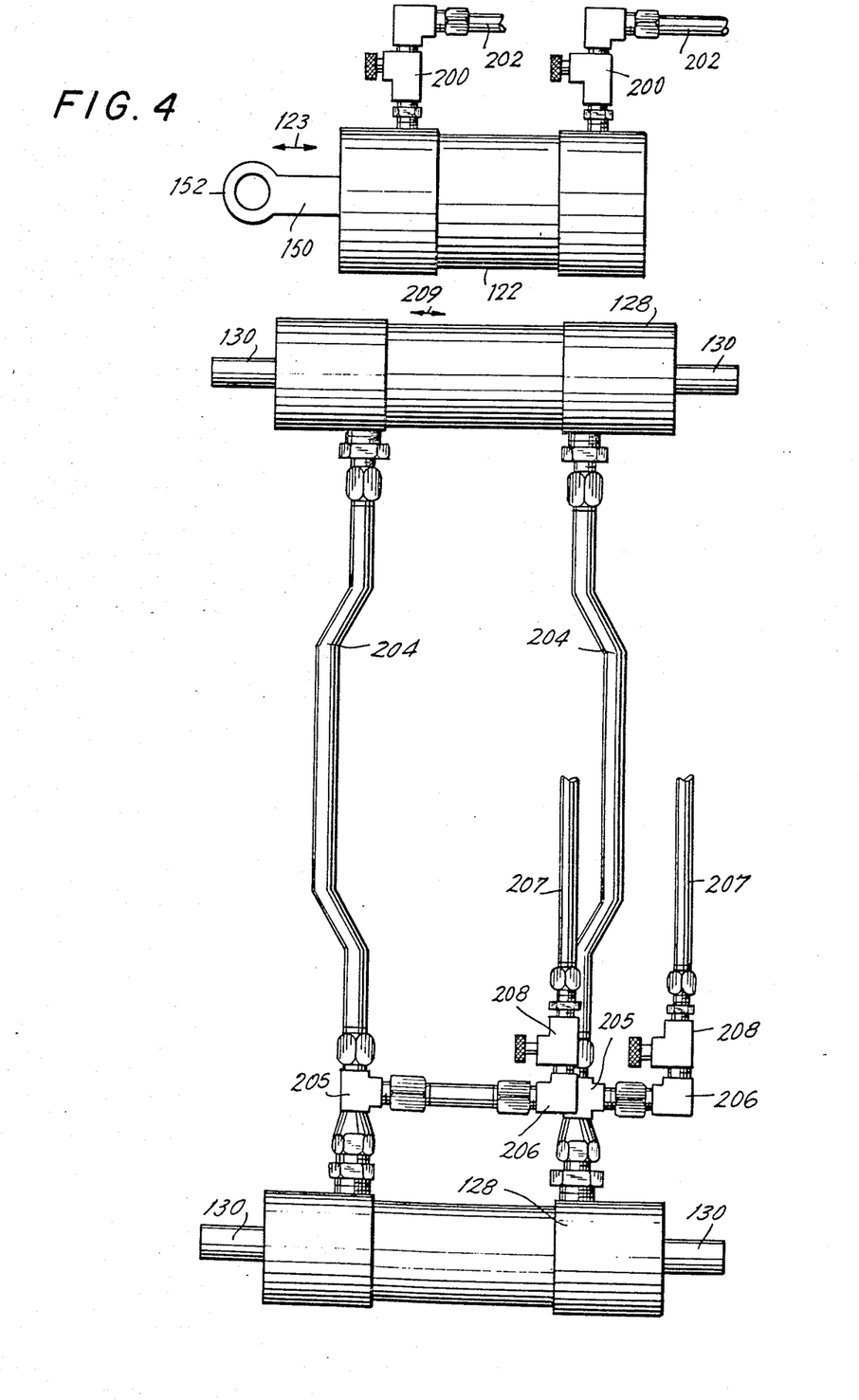
FIG. 4 is a schematic illustrating the hydraulic system of the invention.

The hydraulic controls as illustrated in FIG. 4 are designed to provide the necessary movement in the cant means 119 and positioning means 121. The hydraulic cylinder 122 is connected to the cant means 119 as illustrated in FIG. 1 and includes the outwardly extending cant shaft or piston 150 having a free end 152 that moves in both directions as illustrated by double headed arow 123. To obtain this reciprocation a pair of spaced apart fluid coupling members 200 are attached to opposite ends of the hydraulic cylinder 122. The fluid coupling members 200 may also include bleed valves for bleeding the line as required. Hydraulic lines 202 are connected to the respective fluid coupling members 200 and are connected to hydraulic pumps well known in the art.

The hydraulic pumps in conjunction with the hydraulic lines 202 and fluid coupling members 200 are designed to withstand the forces applied against the carriage 10, and accordingly retain the cant means 119 in fixed operative relationship during travel of the carriage 10.

To assure equal lateral movement of the positioning means 121 at each end of the positioning frame 125, the positioning hydraulic cylinders 128 are utilized and each have a double ended piston shaft 130. The hydraulic cylinder 128 travels along its respective piston rod 130. To be assured that equal travel is obtained, each end of the double acting hydraulic cylinder 128 has fluid coupling means in the form of hydraulic tubing 204 connecting each end thereof together. Interposed between each end of the hydraulic tubing 204 is a coupling tee 205, which is in turn connected to an elbow 206 which is in turn connected to independent hydraulic lines 207. A bleed valve 208 may be interposed between the hydraulic lines 207 and the elbows 206. This arrangement permits hydraulic fluid to either enter or exit from each of the hydraulic lines 207 in such a manner that lateral motion of each of the hydraulic cylinders 128 in the direction of double headed arrow 209 is obtained. Furthermore, the hydraulic system is capable of withstanding pressures normally applied thereto such that the hydraulic cylinder 128 remains in fixed position unless fluid flows in a given direction through the fluid lines associated therewith.

Accordingly, what has hereinabove been described is a new and novel ultrasonic testing system for the testing of flaws and other problems that may be associated with track rail. The device permits the operator complete control and the ability to position the ultrasonic sensing means with complete accuracy and in such a manner that each transducer is independently adjustable with respect to its associated wheel frame. The term "ultrasonic" as used herein is intended to define the frequency range of 5,000 hertz to 50 megahertz.

Although an illustrative embodiment of the invention has been described in detail herein with reference to the accompanying drawings, it is to be understood that the invention is not limited to the precise embodiment and that various changes and modifications may be effected therein without departing from the scope or spirit of the invention.

We claim:

1. An ultrasonic track testing carriage for movement along rails in operative relationship with a test vehicle, comprising:
    A. a pair of wheel frames each having guide means for following the gauge side of the rail and ultrasonic sensing means mounted in working relationship with a portion of the rail for detecting changes in the rail and the position of said sensing means relative to the rail,
    B. a main frame disposed between said wheel frames and adapted to be coupled to the test vehicle for movement therewith, and
    C. interconnecting means between said main frame and each of said wheel frames, said interconnecting means including:
        1. a pair of link members associated with each said wheel frame and said main frame,
        2. means for pivotally mounting each pair of said link members in spaced apart relationship to each other between said wheel frames and said main frame, and
        3. coupling means for pivotally joining each pair of said link members together to provide a connection therebetween so as to permit each said wheel frame independent freedom of motion relative to said main frame in a plane substantially perpendicular to the gauge side of the rail while simultaneously maintaining parallelism between said wheel frames.

2. An ultrasonic track testing carriage as in claim 1, and further including locking means operatively connected between said coupling means and said main frame to lock the position of said wheel frames in place relative to said main frame.

3. An ultrasonic track testing carriage as in claim 2, and further including energizing means operatively associated with said wheel frames to automatically activate said locking means.

4. An ultrasonic track testing carriage as in claim 3, wherein said energizing means is activated when lateral restraint of said wheel frames against the rails is eliminated.

5. An ultrasonic track testing carriage as in claim 1, and further including tow means connected between said main frame and the test vehicle to provide movement of the carriage along the rails.

6. An ultrasonic track testing carriage as in claim 5, wherein said tow means is pivotally mounted to said main frame to permit vertical displacement thereof for removal of the carriage from the rails.

7. An ultrasonic track testing carriage as in claim 6, wherein said tow means is resiliently mounted to said main frame to permit angular movement of said main frame relative to the test vehicle.

8. An ultrasonic track testing carriage as in claim 1, wherein said coupling means includes:
    a. a coupling element connected to and extending outwardly from each of said link members at one end thereof for movement therewith relative to the perpendicular motion of each said wheel frame relative to said main frame, and
    b. a coupling arm pivotally connecting each pair of coupling elements at the other end thereof such that uniform movement of each pair of said link members relative to each other is maintained.

9. An ultrasonic track testing carriage as in claim 8,
    a. wherein said main frame further includes a pair of horizontal spaced apart cross members extending transversely of said main frame,
    b. wherein each said wheel frame includes a pair of inwardly disposed spaced apart link arms,
    c. wherin one surface of said cross members and said link arms are substantially in the same horizontal plane for receiving respective ends of said link members in overlapping relationship thereto, and
    d. wherein the means for pivotally mounting the opposite end of each link member extends through said link arms and said cross members.

10. An ultrasonic track testing carriage as in claim 1, and further including positioning means operatively associated with each of said wheel frames to permit incremental lateral adjustments of said ultrasonic sensing means relative to each rail.

11. An ultrasonic track testing carriage as in claim 1, and further including cant means operatively associated with each of said wheel frames to permit angular adjustment of said ultrasonic sensing means relative to each rail.

12. An ultrasonic track testing carriage as in claim 11, wherein said cant means includes:
    a. a cant frame adapted to be positioned proximate each said wheel frame having an upper end and downwardly extending lower end,
    b. means for mounting said lower end relative to said wheel frame along an axis extending substantially parallel to the rail for angular displacement of said cant frame along said axis,
    c. means for mounting said ultrasonic sensing means in cooperating relation with said cant frame such that said sensing means is angularly adjusted with the movement of said cant frame about said axis, and d. means extending between said wheel frame and said cant frame at said upper end to obtain displacement between said cant frame and said wheel frame so as to obtain the desired angular displacement of said ultrasonic sensing means for proper positioning relative to the portion of the rail being tested.

13. An ultrasonic track testing carriage as in claim 12, wherein said means extending between said wheel frame and said cant frame at said upper end thereof includes:

a. fluid pressure means pivotally connected at one end thereof to said wheel frame, b. a bracket extending from said cant frame, and c. the other end of said fluid pressure means coupled to said bracket, such that linear movement of said fluid pressure means applies the necessary force to obtain the angular displacement of said cant frame relative to said axis.

14. An ultrasonic track testing carriage as in claim 12, and further including positioning means mounted relative to said cant means to permit incremental lateral adjustment of said ultrasonic sensing means relative to said cant frame.

15. An ultrasonic track testing carriage as in claim 14, wherein said positioning means includes:

a. a positioning frame, b. means for mounting said positioning frame relative to said cant frame, wherein said ultrasonic sensing means extends downwardly from said positioning frame, and c. means for lateral displacement of said positioning frame relative to said cant frame to provide incremental lateral adjustment of the contacting surface of said ultrasonic sensing means relative to the rail portion being tested.

16. An ultrasonic track testing carriage as in claim 15, wherein said means for lateral displacement of said positioning frame relative to said cant frame includes:

a. hydraulic means connected to said positioning frame at each end thereof, said hydraulic means having a piston rod extending axially therethrough and outwardly from each end thereof, and b. means for mounting each end of said piston rod in fixed relationship to said cant frame such that said hydraulic means moves laterally along said piston rod to obtain the desired lateral adjusted positionment of the ultrasonic sensing means relative to the rail.

17. An ultrasonic track testing carriage as in claim 16, wherein the hydraulic fluid in said hydraulic means may be controlled so as to retain said positioning frame in relatively fixed position during operation of the carriage.

18. An ultrasonic track testing carriage as in claim 15, and further including means for mounting said ultrasonic sensing means relative to said positioning frame to provide vertical displacement of said ultrasonic sensing means relative to the upper surface of the rail.

19. An ultrasonic track testing carriage as in claim 18, a. wherein said ultrasonic sensing means includes a wheel having a contacting surface for rolling engagement with the rail, and b. wherein said means for mounting said ultrasonic sensing means includes:

1. a downwardly extending bracket rigidly connected to said positioning frame, 2. a support frame including a pair of spaced apart arms with a transversely extending axle extending through said wheel to permit rolling contact with the rail, 3. an upper pivot arm connecting said bracket to the upper end of said arms, and 4. a lower pivot arm connecting said bracket to the lower end of said arms such that vertical displacement of said ultrasonic sensing means is obtained relative to the upper surface of the rail.

20. An ultrasonic track testing carriage as in claim 3, and further including:

a. locking means operatively connected between said coupling means and said main frame to lock the position of said wheel frames in place relative to said main frame, b. energizing means operatively associated with said wheel frames to automatically activate said locking means, and c. switching means operatively associated with said energizing means and mounted relative to said ultrasonic sensing means such that downward movement thereof automatically energizes said switching means such that activation of said locking means locks the position of said wheel frames to prevent lateral movement thereof relative to said main frame.

21. An ultrasonic track testing carriage for movement along rails in operative relationship with a test vehicle, comprising:

A. a pair of wheel frames each having guide means for following the gauge side of the rail, B. a main frame disposed between said wheel frames and adapted to be coupled to the test vehicle for movement therewith, C. interconnecting means between said main frame and each of said wheel frames to provide a connection therebetween so as to permit each said wheel frame independent freedom of motion relative to said main frame in a plane substantially perpendicular to the gauge side of the rail while simultaneously maintaining parallelism between said wheel frames, D. locking means operatively connected between said coupling means and said main frame to lock the position of said wheel frames in place relative to said main frame, E. cant means mounted relative to each said wheel frame for angular displacement relative thereto, F. positioning means mounted relative to each said cant means for lateral displacement relative thereto, G. ultrasonic sensing means having a working surface for positionment adjacent the rail for transmitting an ultrasonic energy pulse into the rail and receiving a reflected ultrasonic energy pulse therefrom, and H. support means for mounting said ultrasonic sensing means relative to each said positioning means to provide vertical displacement of said sensing means relative to said positioning means, such that said sensing means may be adjusted in a vertical, lateral, and angular plane relative to the rail.

22. An ultrasonic track testing carriage as in claim 21, and further including switching means operatively associated with said locking means and mounted relative to said ultrasonic sensing means such that downward movement thereof automatically energizes said switching means such that activation of said locking means locks the position of said wheel frames to prevent lateral movement thereof relative to said main frame.

23. An ultrasonic track testing carriage as in claim 22, and further including skid means connected to and outwardly extending from each of said wheel frames, so as to lift said carriage upwardly from the rails such that said switching means is activated for locking said wheel frames relative to said main frame.

24. An ultrasonic track testing carriage as in claim 22, and further including fluid supply means to maintain a fluid film between said ultrasonic sensing means and the rail.

25. An ultrasonic track testing carriage as in claim 21, wherein said interconnecting means includes:
   1. a pair of link members associated with each said wheel frame and said main frame,
   2. means for pivotally mounting each pair of said link members in spaced apart relationship to each other between said wheel frames and said main frame, and
   3. coupling means for pivotally joining each pair of said link members together to provide a connection therebetween so as to permit each said wheel frame independent freedom of motion relative to said main frame in a plane substantially perpendicular to the gauge side of the rail while simultaneously maintaining parallelism between said wheel frames.

26. An ultrasonic track testing carriage as in claim 25, wherein said coupling means includes:
   a. a coupling element connected to and extending outwardly from each of said link members at one end thereof for movement therewith relative to the perpendicular motion of each said wheel frame relative to said main frame, and
   b. a coupling arm pivotally connecting each pair of said coupling elements at the other end thereof such that uniform movement of each pair of said link members relative to each other is maintained.

27. An ultrasonic track testing carriage as in claim 26,
   a. wherein said main frame further includes a pair of horizontal spaced apart cross members extending transversely of said main frame,
   b. wherein each said wheel frame includes a pair of inwardly disposed spaced apart link arms,
   c. wherein one surface of said cross members and said link arms are substantially in the same horizontal plane for receiving respective ends of said link members in overlapping relationship thereto, and
   d. wherein the means for pivotally mounting the opposite end of each said link member extends through said link arms and said cross members.

28. An ultrasonic track testing carriage as in claim 21, and further including tow means connected between said main frame and the test vehicle to provide movement of the carriage along the rails.

29. An ultrasonic track testing carriage as in claim 28, wherein said tow means is pivotally mounted to said main frame to permit vertical displacement thereof for removal of the carriage from the rails.

30. An ultrasonic track testing carriage as in claim 29, wherein said tow means is resiliently mounted to said main frame to permit angular movement of said main frame relative to the test vehicle.

31. An ultrasonic track testing carriage as in claim 21,
   a. wherein said cant means includes:
      1. a cant frame adapted to be positioned proximate each said wheel frame having an upper end and downwardly extending lower end,
      2. means for mounting said lower end relative to said wheel frame along an axis extending substantially parallel to the rail for angular displacement of said cant frame about said axis, and
      3. means extending between said wheel frame and said cant frame at said upper end to obtain lateral displacement between said cant frame and said wheel frame so as to obtain the desired angular displacement of said ultrasonic sensing means for proper positioning relative to the portion of the rail being tested, and
   b. wherein said positioning means includes:
      4. a positioning frame,
      5. means for mounting said positioning frame relative to said cant frame, wherein said ultrasonic sensing means extends downwardly from said positioning frame, and
      6. means for lateral displacement of said positioning frame relative to said cant frame to provide incremental adjustment of the working surface of said ultrasonic sensing means realtive to the rail portion being tested.

32. An ultrasonic track testing carriage as in claim 31, wherin said means extending between said wheel frame and said cant frame at said upper end thereof includes:
   a. hydraulic means pivotally connected at one end thereof to said wheel frame,
   b. a bracket extending from said cant frame, and
   c. a piston rod axially extending from said hydraulic means having its free end coupled to said bracket, such that linear movement of said piston rod applies the necessary force to obtain the angular displacement of said cant frame relative to said axis.

33. An ultrasonic track testing carriage as in claim 31, wherein said means for lateral displacement of said positioning frame relative to said cant frame includes:
   a. hydraulic means connected to said positioning frame at each end thereof, said hydraulic means having a piston rod extending axially therethrough and outwardly from each end thereof, and
   b. means for mouting each end of said piston rod in fixed relationship to said cant frame such that said hydraulic means moves laterally along said piston rod to obtain the desired lateral adjusted positionment of the ultrasonic sensing means relative to the rail.

34. An ultrasonic track testing carriage as in claim 33, wherein the hydraulic fluid in said hydraulic means may be controlled so as to retain said positioning frame in relatively fixed position during operation of the carriage.

35. An ultrasonic track testing carriage for movement along rails in operative relationship with a test vehicle, comprising:
   A. a pair of wheel frames each having guide means for following the gauge side of the rail,
   B. a main frame disposed between said wheel frames and adapted to be coupled to the test vehicle for movement therewith,
   C. interconnecting means between said main frame and each of said wheel frames, said interconnecting means including:
      1. a pair of link members associated with each said wheel frame and said main frame,
      2. means for pivotally mounting each pair of said link members in spaced apart relationship to each other between said wheel frames and said main frame, and 3. coupling means for pivotally joining each pair of said link members together to provide a connection therebetween so as to permit each said wheel frame independent freedom of motion relative to said main frame in a plane substantially perpendicular to the gauge side of the rail while simultaneously maintaining parallelism between said wheel frames, D. locking means operatively connected between said coupling means and said main frame to lock the position of said wheel frames in place relative to said main frame, E. positioning means including a positioning frame associated with each of said wheel frames, F. cant means including a cant frame mounted relative to each said wheel frame in surrounding relationship to said positioning means, G. ultrasonic sensing means mounted on each of said positioning means having a working surface to be placed in operative relationship with a portion of the rail for transmitting an ultrasonic energy pulse into the rail and receiving a reflected ultrasonic energy pulse therefrom, H. wherein said positioning means includes:
 1. means for mounting each said positioning frame relative to each said cant frame, wherein said ultrasonic sensing means extends downwardly from said positioning frame, and
 2. means for moving said positioning frame relative to said cant frame to provide incremental lateral adjustment of the working surface of said ultrasonic sensing means relative to the rail portion being tested, I. wherein said cant means includes:
 3. means for mounting the lower end of said cant frame relative to said wheel frame along an axis extending substantially parallel to the rail for angular displacement of said cant frame along said axis, and
 4. means extending between said wheel frame and said cant frame at the upper end thereof to obtain lateral displacement between said cant frame and said wheel frame so as to obtain the desired angular displacement of said ultrasonic sensing means for proper positioning relative to the portion of the rail being tested, and J. switching means operatively associated with said ultrasonic sensing means such that downward movement thereof automatically energizes said switching means such that activation of said locking means locks the position of said wheel frames to prevent lateral movement thereof relative to said main frame.

36. An ultrasonic track testing carriage as in claim 35, wherein said coupling means includes:
a. a coupling element connected to and extending outwardly from each of said link members at one end thereof for movement therewith relative to the perpendicular motion of each said wheel frame relative to said main frame, and
b. a coupling arm pivotally connecting each pair of coupling elements at the other end thereof such that uniform movement of each pair of said link members relative to each other is maintained.

37. An ultrasonic track testing carriage as in claim 36,
a. wherein said main frame further includes a pair of horizontal spaced apart cross members extending transversely of said main frame,
b. wherein each said wheel frame includes a pair of inwardly disposed spaced apart link arms,
c. wherein one surface of said cross members and said link arms are substantially in the same horizontal plane for receiving respective ends of said link members in overlapping relationship thereto, and
d. wherein the means for pivotally mounting the opposite end of each said link member extends through said link arms and said cross members.

38. An ultrasonic track testing carriage as in claim 35, and further including tow means connected between said main frame and the test vehicle to provide movement of the carriage along the rails.

39. An ultrasonic track testing carriage as in claim 38, wherein said tow means is pivotally mounted to said main frame to permit vertical displacement thereof for removal of the carriage from the rails.

40. An ultrasonic track testing carriage as in claim 39, wherein said tow means is resiliently mounted to said main frame to permit angular movement of said main frame relative to the test vehicle.

41. An ultrasonic track testing carriage as in claim 40, wherein said means extending between said wheel frame and said cant frame at said upper end thereof includes:
a. fluid pressure means pivotally connected at one end thereof to said wheel frame,
b. a bracket extending from said cant frame, and
c. the other end of said fluid pressure means coupled to said bracket, such that linear movement of said fluid pressure means applies the necessary force to obtain the angular displacement of said cant frame relative to said axis.

42. An ultrasonic track testing carriage as in claim 35, wherein said means for lateral displacement of said positioning frame relative to said cant frame includes:
a. hydraulic means connected to said positioning frame at each end thereof, said hydraulic means having a piston rod extending axially therethrough and outwardly from each end thereof, and
b. means for mounting each end of said piston rod in fixed relationship to said cant frame such that said hydraulic means moves laterally along said piston rod to obtain the desired lateral adjusted positionment of the ultrasonic sensing means relative to the rail.

43. An ultrasonic track testing carriage as in claim 42, wherein the hydraulic fluid in said hydraulic means may be controlled so as to retain said positioning frame in relatively fixed position during operation of the carriage.

44. An ultrasonic track testing carriage as in claim 43, and further including means for mounting said ultrasonic sensing means relative to said positioning frame to provide vertical displacement of said ultrasonic sensing means relative to the upper surface of the rail.

45. An ultrasonic track testing carriage as in claim 35:
a. wherein said ultrasonic sensing means includes a wheel having a working surface for rolling engagement with the rail, and
b. further including means for mounting said ultrasonic sensing means relative to said positioning means, said means including:
 1. a downwardly extending bracket rigidly connected to said positioning frame,
 2. a support frame including a pair of spaced apart arms with a transversely extending axle extending through said wheel to permit rolling contact with the rail,
3. an upper pivot arm connecting said bracket to the upper end of said arms, and
4. a lower pivot arm connecting said bracket to the lower end of said arms such that vertical displacement of said ultrasonic sensing means is obtained relative to the upper surface of the rail.

46. An ultrasonic track testing carriage as in claim 35, and further including skid means outwardly extending from each of said wheel frames and positioned relative thereto so as to vertically lift the wheel frames and said main frame upwardly from the rails upon engagement with a foreign object, so as to activate said switching means.

47. A method of ultrasonic track testing comprising the steps of:
A. moving a carriage along rails in operative relationship with a test vehicle, said carriage including a pair of wheel frames each having guide means to follow the gauge side of the rail, with a main frame disposed between said wheel frames and adapted to be coupled to the test vehicle for movement therewith,
B. interconnecting said main frame and each of said wheel frames to provide a coupling therebetween so as to permit each said wheel frame independent freedom of motion relative to said main frame in a plane substantially perpendicular to the gauge side of the rail while simultaneously maintaining parallelism between said wheel frames,
C. transmitting an ultrasonic energy pulse into the rail from ultrasonic sensing means adjustably mounted relative to each of said wheel frames and receiving a reflected ultrasonic energy pulse from the rail, and
D. adjusting said ultrasonic sensing means relative to each said wheel frame, whereby the axis of said ultrasonic energy pulse may be adjusted in a vertical, lateral and angular plane relative to the rail.

48. A method of ultrasonic track testing as in claim 47, and further including the step of locking said wheel frames in place relative to said main frame.

49. A method of ultrasonic track testing as in claim 48, and further including the step of automatically locking said wheel frame in place relative to said main frame when said wheel frame is lifted from the rail.

50. A method of ultrasonic track testing as in claim 47, wherein said step of adjusting said ultrasonic sensing means relative to each said wheel frame includes the steps of:
a. mounting a cant frame for each said wheel frame, said cant frame having a lower end mounted relative to said wheel frame along an axis extending substantially parallel to the rail for angular adjustment along said axis,
b. moving the upper end of said cant frame until the desired angular position of said ultrasonic sensing means relative to the rail is obtained,
c. suspending a positioning frame from each of said cant frames from which positioning frame said ultrasonic sensing means extends downwardly therefrom, and
d. adjusting the lateral position of each said positioning frame relative to said cant frame until the desired reflected ultrasonic energy pulse is received.

* * * * *